(12) United States Patent
Stoddard et al.

(10) Patent No.: US 10,729,458 B2
(45) Date of Patent: Aug. 4, 2020

(54) ULTRASONIC SURGICAL INSTRUMENTS

(75) Inventors: Robert B. Stoddard, Steamboat Springs, CO (US); James S. Cunningham, Boulder, CO (US); William J. Dickhans, Longmont, CO (US); Russell D. Hempstead, Lafayette, CO (US); Eric R. Larson, Boulder, CO (US); Duane E. Kerr, Loveland, CO (US); William H. Nau, Longmont, CO (US); Anthony B. Ross, Boulder, CO (US); John J. Kappus, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 886 days.

(21) Appl. No.: 14/006,601

(22) PCT Filed: Mar. 30, 2012

(86) PCT No.: PCT/US2012/031585
§ 371 (c)(1),
(2), (4) Date: Sep. 20, 2013

(87) PCT Pub. No.: WO2012/135705
PCT Pub. Date: Oct. 4, 2012

(65) Prior Publication Data
US 2014/0012299 A1 Jan. 9, 2014

Related U.S. Application Data

(60) Provisional application No. 61/469,588, filed on Mar. 30, 2011.

(51) Int. Cl.
*A61B 17/32* (2006.01)
*A61B 17/00* (2006.01)
(Continued)

(52) U.S. Cl.
CPC ............... *A61B 17/320092* (2013.01); *A61B 2017/00022* (2013.01); *A61B 2017/00026* (2013.01);
(Continued)

(58) Field of Classification Search
CPC .......... A61B 17/320068; A61B 17/295; A61B 17/320092; A61B 2090/034;
(Continued)

(56) References Cited

U.S. PATENT DOCUMENTS 3,076,904 A  2/1963  Kleesattel et al.
6,454,781 B1  9/2002  Witt et al.
(Continued)

FOREIGN PATENT DOCUMENTS

DE  3507672 A1  9/1986
DE  3630478 C1  1/1988
(Continued)

OTHER PUBLICATIONS

European Search Report, Application No. EP 12 76 5108 dated Mar. 26, 2015.
(Continued)

*Primary Examiner* — Erich G Herbermann
(74) *Attorney, Agent, or Firm* — Carter, DeLuca & Farrell LLP

(57) ABSTRACT

An ultrasonic surgical instrument is provided. The ultrasonic surgical instrument includes a housing having an elongated shaft extending therefrom. The shaft has a jaw member disposed at a distal end thereof. The jaw member is movable between an open configuration and a clamping configuration and includes a tissue contacting surface thereon. A cutting blade extends from a distal end of the shaft and operably couples to the housing and adjacent the jaw member to treat tissue. At least one sensor is configured to sense at least one
(Continued)

operational parameter of the ultrasonic surgical instrument. At least one controller in operable communication with the at least one sensor is configured to terminate delivery of ultrasonic energy to the cutting blade when the at least one sensor senses the at least one operational parameter.

20 Claims, 2 Drawing Sheets

(51) Int. Cl.
  *A61B 17/28* (2006.01)
  *A61B 90/00* (2016.01)
(52) U.S. Cl.
  CPC .......... *A61B 2017/00115* (2013.01); *A61B 2017/00123* (2013.01); *A61B 2017/00734* (2013.01); *A61B 2017/2825* (2013.01); *A61B 2017/320093* (2017.08); *A61B 2017/320094* (2017.08); *A61B 2090/034* (2016.02); *A61B 2090/064* (2016.02); *A61B 2090/065* (2016.02)
(58) Field of Classification Search
  CPC ....... A61B 2090/064–065; A61B 2017/00123; A61B 2017/00022; A61B 2017/00115; A61B 2017/00734; A61B 2017/00026; A61B 2017/2825
  USPC ............ 606/169; 600/437, 442, 446; 604/22
  See application file for complete search history.

(56) References Cited

U.S. PATENT DOCUMENTS

| | | | |
|---|---|---|---|
| 6,669,690 B1 | 12/2003 | Okada et al. | |
| 7,108,695 B2 | 9/2006 | Witt et al. | |
| 7,431,728 B2* | 10/2008 | Gerry et al. | 606/169 |
| 8,258,886 B2 | 9/2012 | Gilbert | |
| 8,373,572 B2 | 2/2013 | Dycus | |
| 8,662,745 B2 | 3/2014 | Misuchenko et al. | |
| 8,665,031 B2 | 3/2014 | Gilbert | |
| 2002/0183774 A1 | 12/2002 | Witt et al. | |
| 2004/0193198 A1 | 9/2004 | Cuny | |
| 2006/0116610 A1 | 6/2006 | Hare et al. | |
| 2007/0173872 A1* | 7/2007 | Neuenfeldt | 606/169 |
| 2009/0030437 A1 | 1/2009 | Houser et al. | |
| 2009/0036913 A1 | 2/2009 | Wiener et al. | |
| 2009/0036914 A1* | 2/2009 | Houser | A61B 17/29 606/169 |
| 2009/0259243 A1 | 10/2009 | Tahara et al. | |
| 2009/0326437 A1* | 12/2009 | Beerwerth | A61B 18/203 604/20 |
| 2010/0168572 A1* | 7/2010 | Sliwa | A61B 8/0833 600/439 |
| 2010/0312111 A1 | 12/2010 | Tanaka et al. | |
| 2010/0331742 A1* | 12/2010 | Masuda | 601/2 |
| 2010/0331838 A1 | 12/2010 | Ibrahim et al. | |
| 2011/0004233 A1* | 1/2011 | Muir et al. | 606/169 |
| 2011/0213391 A1* | 9/2011 | Rivers et al. | 606/159 |
| 2012/0046659 A1* | 2/2012 | Mueller | 606/41 |
| 2013/0127625 A1 | 5/2013 | Dycus | |
| 2013/0197511 A1 | 8/2013 | Balanev et al. | |
| 2013/0231664 A1 | 9/2013 | Balanev et al. | |
| 2013/0325047 A1 | 12/2013 | Craig | |
| 2013/0331873 A1 | 12/2013 | Ross et al. | |
| 2013/0331874 A1 | 12/2013 | Ross et al. | |
| 2013/0331875 A1 | 12/2013 | Ross et al. | |
| 2014/0012297 A1 | 1/2014 | Ross et al. | |
| 2014/0012298 A1 | 1/2014 | Cunningham et al. | |
| 2014/0012299 A1 | 1/2014 | Stoddard et al. | |
| 2014/0017118 A1 | 1/2014 | Stoddard et al. | |

FOREIGN PATENT DOCUMENTS

| | | | | |
|---|---|---|---|---|
| DE | 10141385 A1 | 7/2002 | | |
| DE | 20118698 U1 | 4/2003 | | |
| DE | 20118699 U1 | 4/2003 | | |
| DE | 20303776 U1 | 7/2004 | | |
| EP | 0 741 996 A2 | 11/1996 | | |
| EP | 1820460 A2 | 8/2007 | | |
| EP | 2314235 A2 | 4/2011 | | |
| GB | WO 2011036485 A1 * | 3/2011 | ............... A61B 8/00 | |
| JP | 61096419 A | 5/1986 | | |
| JP | 02034008 A | 2/1990 | | |
| JP | 06114069 A | 4/1994 | | |
| JP | 2001212514 A | 8/2001 | | |
| JP | 2001346805 A | 12/2001 | | |
| JP | 2002045368 A | 2/2002 | | |
| JP | 2002186901 A | 2/2002 | | |
| JP | 2002-237204 | 8/2002 | | |
| JP | 2004254128 A | 9/2004 | | |
| JP | 3696034 B2 | 7/2005 | | |
| JP | 3756726 B2 | 1/2006 | | |
| JP | 2008-188160 A | 8/2008 | | |
| WO | WO 2005/122917 A1 | 12/2005 | | |
| WO | WO 2006/101644 A2 | 9/2006 | | |
| WO | WO 2007/014548 A2 | 2/2007 | | |
| WO | WO 2008/012357 A1 | 1/2008 | | |
| WO | WO 2008/012359 A1 | 1/2008 | | |
| WO | WO 2008/051764 A2 | 5/2008 | | |
| WO | WO 2008/065323 A1 | 6/2008 | | |
| WO | WO 2008/118709 A1 | 10/2008 | | |
| WO | 201108672 A2 | 1/2011 | | |
| WO | 2012061739 A1 | 5/2012 | | |

OTHER PUBLICATIONS

Extended European Search Report for EP 12 76 5108 dated Aug. 7, 2015.

* cited by examiner

ULTRASONIC SURGICAL INSTRUMENTS

CROSS-REFERENCE TO RELATED APPLICATION

The present application claims the benefit of and priority to U.S. Provisional Application No. 61/469,588 filed on Mar. 30, 2011 by Stoddard et al., the entire contents of which is incorporated herein by reference.

BACKGROUND

1. Technical Field

The present disclosure relates to ultrasonic surgical instruments. More particularly, the present disclosure relates to ultrasonic surgical instruments having one or more sensor configurations to prevent wear of tissue contacting surfaces on jaw members of the ultrasonic surgical instrument.

2. Description of Related Art

Ultrasonic energy-powered instruments configured to cut and/or fragment tissue are known in the art. Ultrasonic instruments, typically, include a transducer that is coupled to a probe/waveguide having an active member (e.g., cutting blade, shear, hook, ball, etc.) at a distal end thereof. In use, ultrasonic energy is utilized to vibrate (e.g., at frequency usually in the range of 20 KHz to 60 KHz) the active member to treat tissue of interest.

Ultrasonic instruments may include any of a variety of probe configurations to achieve a specific surgical result. For example, the probe configuration may include an active member in the form of a cutting blade that is combined with a movable jaw configured to grasp and/or manipulate tissue. In certain instances, a tissue contacting surface (which is typically made from metal) of the movable jaw member may include a polytetrafluoroethylene (PTFE) liner configured to prevent the cutting blade from coming into contact with the tissue contacting surface. Such ultrasonic instruments are primarily used in a variety of medical procedures including open surgical procedures, luminal procedures, and endoscopic procedures.

During use, the movable jaw member provides support for tissue as the cutting blade vibrates to treat tissue. The PTFE liner and/or the tissue contacting surface of the movable jaw member may wear as a result of prolonged use. As can be appreciated, wear of the PTFE liner and/or the tissue contacting surface of the movable jaw member may result in a decreased surgical effect to tissue. That is, as the PTFE liner and/or tissue contacting surface wears, its tissue supporting capabilities may be diminished.

SUMMARY

In view of the foregoing, ultrasonic instruments including one or more sensor configurations to prevent wear of tissue contacting surfaces on jaw members of the ultrasonic surgical instrument may prove useful in the medical art.

Embodiments of the present disclosure are described in detail with reference to the drawing figures wherein like reference numerals identify similar or identical elements. As used herein, the term "distal" refers to a portion that is being described which is further from a user, while the term "proximal" refers to a portion that is being described which is closer to a user.

An aspect of the present disclosure provides an ultrasonic surgical instrument. The ultrasonic instrument includes a housing having an elongated shaft extending therefrom. The shaft includes a jaw member disposed at a distal end thereof. The jaw member is movable between an open configuration and a clamping configuration and includes a tissue contacting surface. A cutting blade extends from a distal end the shaft and operably couples to the housing and adjacent the jaw member to treat tissue. At least one sensor is configured to sense at least one operational parameter of the ultrasonic surgical instrument. At least one controller in operable communication with the at least one sensor is configured to terminate delivery of ultrasonic energy to the cutting blade when the at least one sensor senses the at least one operational parameter. The controller may be a component of a generator of the ultrasonic surgical instrument.

The at least one sensor may be operably coupled to at least one of the jaw member or cutting element. The at least one sensor may be a position sensor, a strain gauge sensor, jaw sensor, a temperature sensor, an acoustic sensor or an impedance sensor.

The at least one operational parameter associated with the ultrasonic surgical instrument may include a change in tissue impedance of tissue being treated, a change in resistance associated with the cutting blade contacting the tissue contacting surface of the jaw member, a change in an acoustic signature of the ultrasonic surgical associated with the cutting blade vibrating against the tissue contacting surface of the jaw member, a change in an amount of ultrasonic power required to treat tissue, a spatial relationship between the jaw member and cutting blade, a change in contact pressure between the jaw member and the cutting blade.

The tissue contacting surface of the jaw member may be coated with at least one lubricious material. The at least one lubricious material may be polytetrafluoroethylene and/or silicone.

The ultrasonic surgical instrument may also include a jaw interlock that is activatable when delivery of ultrasonic energy to the cutting blade is terminated. The jaw interlock may be configured to engage at least one of the jaw member or cutting blade to prevent physical contact therebetween.

An aspect of the present disclosure provides an ultrasonic surgical system. The ultrasonic surgical system includes an ultrasonic surgical instrument. The ultrasonic surgical instrument includes a housing having a shaft extending therefrom. The shaft includes a jaw member disposed at a distal end thereof. The jaw member includes a tissue contacting surface. A cutting blade extends from a distal end of the shaft and operably couples to the housing and adjacent the jaw member to treat tissue. At least one sensor is configured to sense at least one operational parameter of the ultrasonic surgical instrument. At least one controller in operable communication with the at least one sensor is configured to terminate delivery of ultrasonic energy to the cutting blade when the at least one sensor senses the at least one operational parameter, and/or senses a change of the at least one operational parameter. The controller may be a component of a generator of the ultrasonic surgical instrument. The controller may be configured to provide one of an audio and visual indication to a user when the operational parameter, and/or a change thereof, is sensed by the at least one sensor.

The at least one sensor may be operably disposed on at least one of the jaw member or cutting element. The at least one sensor may be a position sensor, a strain gauge sensor, jaw sensor, a temperature sensor, an acoustic sensor, or an impedance sensor.

The ultrasonic surgical instrument may also include a jaw interlock that is activatable when delivery of ultrasonic energy to the cutting blade is terminated. The jaw interlock may be configured to engage at least one of the jaw member or cutting blade to prevent physical contact therebetween. The jaw interlock may be manually activatable via a switching mechanism on the ultrasonic surgical instrument. Alternatively, the jaw interlock may be automatically activatable via the controller.

The at least one operational parameter associated with the ultrasonic surgical instrument may include a change in tissue impedance of tissue being treated, a change in resistance associated with the cutting blade contacting the tissue contacting surface of the jaw member, a change in an acoustic signature of the ultrasonic surgical associated with the cutting blade vibrating against the tissue contacting surface of the jaw member, a change in an amount of ultrasonic power required to treat tissue, a spatial relationship between the jaw member and cutting blade, a change in contact pressure between the jaw member and the cutting blade.

The controller may be in operable communication with an audio detection module of the generator. The audio detection module may be configured to receive audio input from a sensor (e.g., a microphone, transducer, or the like) on the ultrasonic surgical instrument to detect the change in the acoustic signature of the ultrasonic surgical.

The tissue contacting surface of the jaw member may be coated with at least one lubricious material. The at least one lubricious material may be polytetrafluoroethylene and/or silicone.

BRIEF DESCRIPTION OF THE DRAWINGS

Various embodiments of the present disclosure are described hereinbelow with reference to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
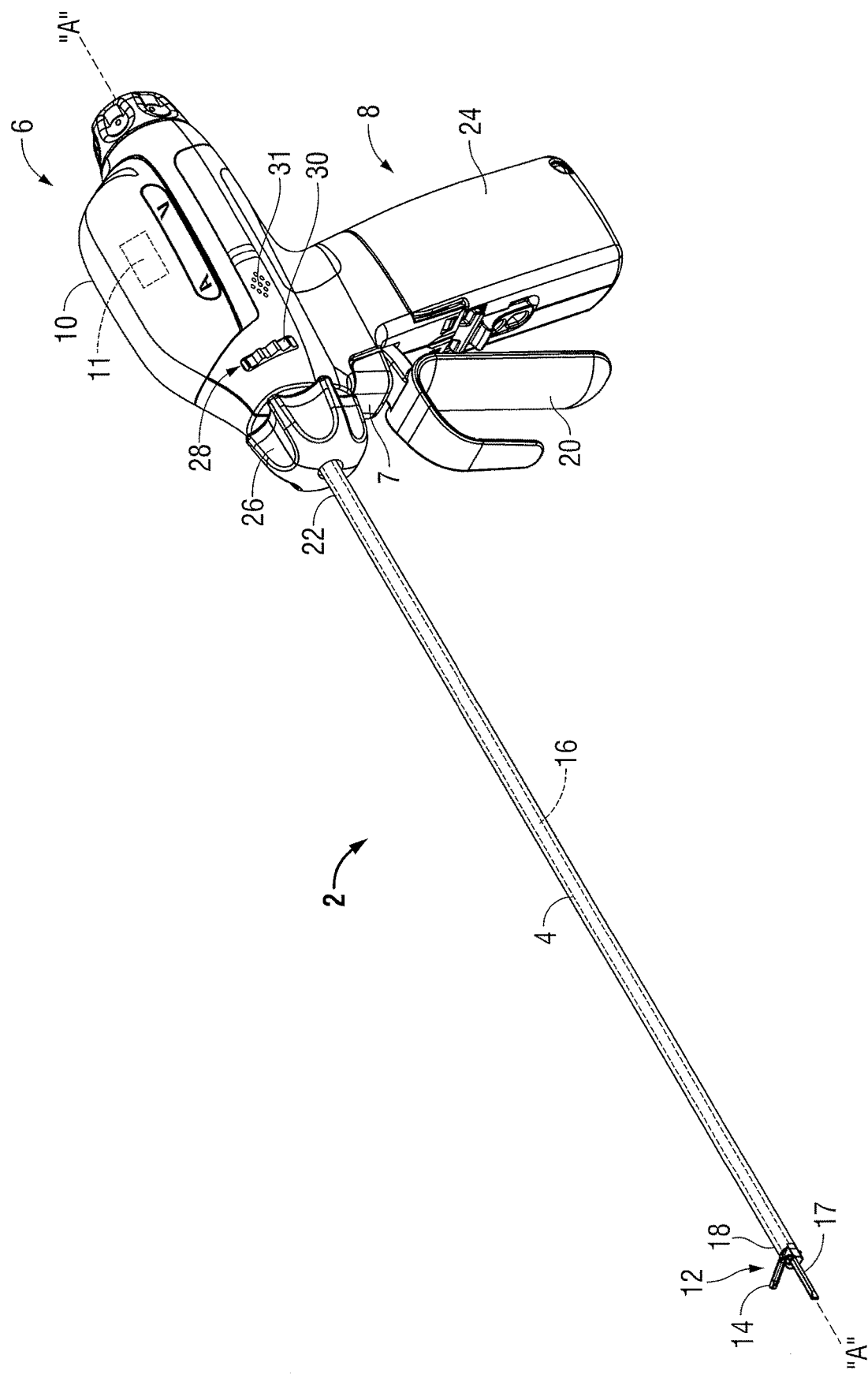
FIG. 1 is a right, perspective view of an ultrasonic instrument according to an embodiment of the present disclosure.

Turning now to FIG. 1, an ultrasonic surgical instrument 2 (instrument 2) according to an embodiment of the present disclosure is illustrated. In the illustrated embodiments, instrument 2 is described herein as being battery powered. Alternatively, instrument 2 may be externally powered, e.g., via a remote ultrasonic generator that couples to instrument 2. In the latter instance, a cable may couple instrument 2 to the generator.

Briefly, instrument 2 includes a housing 6 configured to house one or more components, e.g., transducer (not explicitly shown), a probe 16, and electrical circuitry that is configured for electrical communication with a battery assembly 8 of instrument 2. A proximal end of housing 6 is configured to releasably couple to an ultrasonic generator 10 and battery assembly 8. A distal end of housing 6 is configured to support and/or couple to a proximal end 22 of a shaft 4 having a longitudinal axis "A-A" defined therethrough. A rotation knob 26 operably couples to housing 6 and is configured to rotate shaft 4 approximately 360° in either direction about the longitudinal axis "A-A." Generator 10 includes the transducer that is coupled to probe 16 via a torque adapter (not explicitly shown) and configured to produce vibratory motion of a cutting blade 17 (FIGS. 1-2) disposed at a distal end of probe 16 when a trigger 7 is depressed. This vibratory motion of cutting blade 17 is utilized to treat tissue of interest. Battery assembly 8 includes a handpiece 24 having a battery (not explicitly shown) operably disposed therein.

Figure 2:
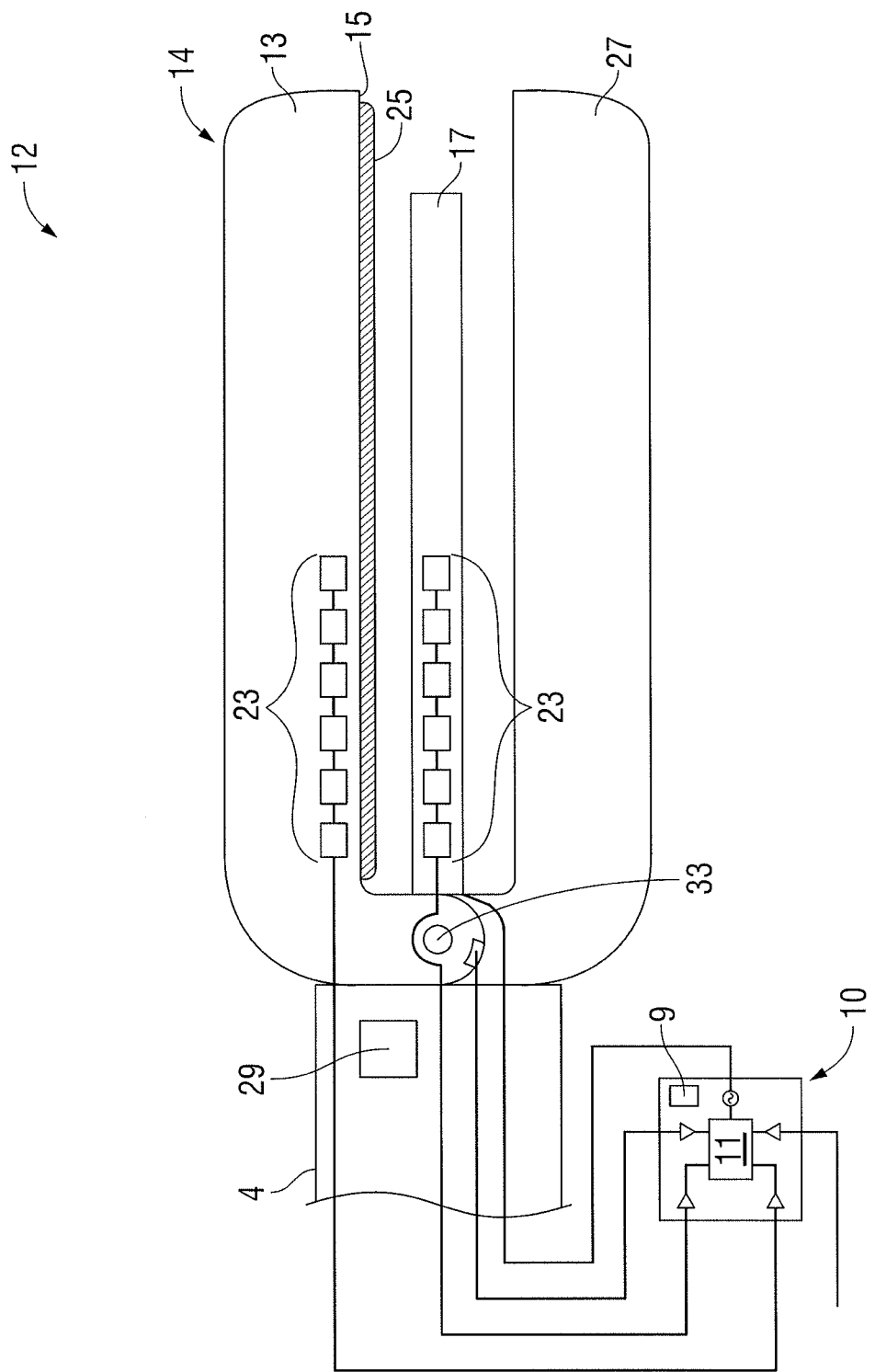
FIG. 2 is an enlarged side, schematic view of a generator, a jaw member and a cutting blade in accordance with the embodiment depicted in FIG. 1.

With reference to FIGS. 1-2, an end effector 12 includes a first jaw member 14 (FIG. 1) that is supported at a distal end 18 of shaft 4 adjacent cutting blade 17. Jaw member 14 may be pivotably supported at the distal end of the shaft 4 via a pivot pin 23 and functions as a "clamping jaw." In particular, jaw member 14 is movable relative to cutting blade 17 (and/or the distal end 18 of the shaft 4) between an open configuration (FIG. 1) and a clamping configuration (FIG. 2) to clamp tissue when a lever or movable handle 20 (FIG. 1) is actuated. Jaw member 14 and cutting blade 17 are configured to collectively grasp and ultrasonically treat tissue. In particular, with tissue positioned between jaw member 14 and cutting blade 17, the cutting blade is configured to vibrate at a specific frequency (e.g., at a frequency in the range from about 20 KHz to about 60 KHz) to treat tissue.

Continuing with reference to FIG. 2, jaw member 14 is illustrated including a jaw housing 13 having a tissue contacting surface 15 operably coupled thereto. Tissue contacting surface 15 provides a compliant, temperature resistant and low friction surface for cutting blade 17 when the jaw member 14 is in the clamping configuration and cutting blade 17 is treating tissue, i.e., vibrating.

In the embodiment illustrated in FIGS. 1-2, tissue contacting surface 15 is provided with a laminate liner 25 that is flexible (or compliant). In the illustrated embodiment, laminate liner 25 includes one or more lubricious materials thereon, e.g., polytetrafluoroethylene, silicone, and the like. Alternatively, tissue contacting surface 15 may be provided without a laminate liner 25. The specific configuration of tissue contacting surface 15 (i.e., with or without a laminate liner 25) may depend on a specific type of tissue that is to be treated, a manufacturer's preference, a specific surgical procedure, a specific type of instrument 2, and so forth.

In an embodiment, it may prove useful to provide a second jaw member 27 (shown in phantom in FIG. 2). In this particular embodiment, second jaw member 27 may include one or more laminate liners 25 (and operative components associated therewith) thereon configured to provide the same function as described above with respect to jaw member 14. Jaw member 27 may be configured similar to jaw member 14 to provide the same functions described herein.

With reference again to FIGS. 1-2, cutting blade 17 is configured to treat tissue of interest and may be formed from any suitable material, including but not limited to metal, ceramic, or other suitable material. In the illustrated embodiments, cutting blade 17 may be formed from stainless steel or titanium. Metals of this type are suitable for forming cutting blade 17 because of their ability to withstand high temperatures and vibrations that are, typically, associated with cutting blade 17 during operation thereof.

Continuing with reference to FIG. 2, one or more sensors 23 (FIG. 2) may be positioned on jaw member 14 and/or cutting blade 17. In the embodiment illustrated in FIG. 2, for example, a plurality of sensor(s) 23 is positioned on both the jaw member 14 and cutting blade 17 and are configured to detect one or more operational parameters associated with instrument 2. In particular, the sensed operational parameters associated with instrument 2 are communicated to a controller 11 and utilized to prevent cutting blade 17 from coming into contact with tissue contacting surface 15 of jaw member 14 and/or coming into contact with laminate liner 25 that may disposed on jaw member 14, e.g., controller 11 triggers an end-of-duty cycle command to terminate ultrasonic energy to cutting blade 17.

The operational parameters associated with instrument 2 include, but are not limited to a change in tissue impedance of tissue being treated, a change in resistance associated with cutting blade 17 contacting tissue contacting surface 15 of jaw member 14, a change in an acoustic signature associated with instrument 2 as a result of cutting blade 17 vibrating against tissue contacting surface 15 of jaw member 14, a change in an amount of ultrasonic power required to treat tissue, a spatial relationship between jaw member 14 and cutting blade 17, a change in contact pressure between jaw member 14 and the cutting blade 17, or a combination thereof.

Accordingly, sensor(s) 23 may be a position sensor, a strain gauge sensor, a jaw sensor, a temperature sensor, an acoustic sensor, an impedance sensor, or any combination thereof. (FIG. 2). As can be appreciated, one or more of the sensor(s) 23 may be positioned on one or both jaw members 14 and/or cutting blade 17.

In some embodiments, for example, a sensor 23 may be configured to sense impedance of tissue as tissue is being treated. In this embodiment, sensor 23 may be positioned on jaw member 14 and cutting blade 17, and configured to communicate one or more of the sensed parameters associated with an impedance of tissue, e.g., resistivity of tissue tends to increase during ultrasonic treatment thereof. In this instance, sensor 23 may be configured to provide an interrogatory pulse through tissue and sense a reflective wave reflected therefrom. One or more properties associated with the reflective wave may be utilized by controller 11 to determine tissue impedance. If the sensed impedance exceeds a predetermined threshold, controller 11 may terminate delivery of ultrasonic energy to cutting blade 17.

Additionally, or alternatively, sensor 23 may be positioned on jaw member 14 and cutting blade 17, and configured to communicate one or more sensed parameters associated with jaw member 14 and cutting blade 17, e.g., resistivity between jaw member 14 and cutting blade 17. For example, in this instance, known resistivity (which may be obtained by any suitable means, e.g., empirically) between jaw member 14 and cutting blade 17 when jaw member 14 is in the clamping and open configurations may be utilized to determine a proximity of jaw member 14 with respect to cutting blade 17. If the sensed resistivity exceeds a predetermined threshold, controller 11 may terminate delivery of ultrasonic energy to cutting blade 17.

Additionally, or alternatively, sensor 23 may be utilized to determine the proximity of jaw member 14 with respect to cutting blade 17 to facilitate preventing cutting blade 17 from contacting tissue contacting surface 15 of jaw member 14 and/or coming into contact with laminate liner 25 that may disposed on jaw member 14. If the sensed distance between tissue contacting surface 15 and cutting blade 17 is below a predetermined threshold, controller 11 may terminate delivery of ultrasonic energy to cutting blade 17.

Additionally, or alternatively, sensor 23 may be utilized to detect a pressure between jaw member 14 and cutting blade 17 to facilitate preventing cutting blade 17 contacting tissue contacting surface 15 of jaw member 14 and/or coming into contact with laminate liner 25 that may disposed on jaw member 14. In this instance, known closure forces (which may be obtained by any suitable means, e.g., empirically) between jaw member 14 and cutting blade 17 when jaw member 14 is in the clamping configuration and tissue is positioned therebetween may be utilized to determine proximity of jaw member 14 with respect to cutting blade 17. In this particular instance, closure forces may be correlated for specific tissue structure, e.g., large vessels, medium vessels, etc. If the sensed closure force between tissue contacting surface 15 and cutting blade 17 exceeds or falls below a predetermined threshold, controller 11 may terminate delivery of ultrasonic energy to cutting blade 17.

Additionally, or alternatively, sensor 23 may be utilized to determine a temperature of tissue contacting surface 15 (and/or laminate liner 25). In this particular instance, a specific temperature (or an increase in temperature) of tissue contacting surface 15 (and/or laminate liner 25) sensed by sensor 23 may be indicative of a proximity of cutting blade 17 with respect to tissue contacting surface 15 (and/or laminate liner 25). For example, a sensed temperature of about 200° C. may correlate to cutting blade 17 being in close proximity to tissue contacting surface 15 (and/or laminate liner 25) and may trigger termination of ultrasonic energy to cutting blade 17.

Additionally, or alternatively, sensor 23 may be utilized to determine a change in an acoustic signature associated with instrument 2 as a result of cutting blade 17 vibrating against tissue contacting surface 15 of jaw member 14. In this instance, the acoustic signature may be the sound produced by cutting blade 17 treating tissue; this sound, e.g., acoustic signature, may be stored into memory of controller 11. During operation of cutting blade 17, sensor 23 may be configured to detect the sound produced by cutting blade 17 and provide the sound to controller 11 for comparison with the acoustic signature stored in memory. If the sound provided to controller 11 does not match the stored acoustic signature, controller 11 may trigger termination of ultrasonic energy to cutting blade 17. Additionally, or alternatively, a speaker 31 (FIG. 1) may be provided on instrument 2 to detect a change in an acoustic signature associated with instrument 2, described in more detail below.

Sensor(s) 23 may be configured to communicate with one or more modules of the generator 10 and/or the battery assembly 8. In one particular embodiment, for example, sensor(s) 23 may be configured to provide data pertaining to one or more of the aforementioned operational parameters associated with instrument 2 to controller 11 (FIG. 2). Controller 11 may be a component associated with generator 10 and/or battery assembly 8. In the illustrated embodiments, controller 11 is provided as a component of the generator 10 (FIG. 2) and analyzes the data pertaining to the aforementioned operational parameters and utilizes one or more control algorithms to control, e.g., terminate, an output response of the transducer based on this data to ensure that cutting blade 17 does not contact tissue contacting surface 15 (and/or laminate liner 25). In one particular embodiment, instrument 2 and controller 11 may be configured to provide one or more indications, e.g., an audio indication "A", a visual indication "V", and so forth, to a user indicating an end-of-duty cycle of instrument 2.

An audio detection module 9 (FIG. 2) may be configured to receive an audio signal from speaker 31 (FIG. 1) and communicate the detected audio signal to controller 11. Controller 11 may analyze the detected audio signal and trigger an end-of-duty cycle command in a manner as described above.

In embodiments, a jaw interlock 29 (FIG. 2) that is activatable when delivery of ultrasonic energy to cutting blade 17 is terminated may be configured to engage one or both of jaw member 14 or cutting blade 17 to prevent inadvertent contact between cutting blade 17 and tissue contacting surface 15 (and/or laminate liner 25). To this end, jaw interlock 29 may be in operable communication with controller 11 and/or a switching mechanism 28 (FIG. 1) and may include any suitable components including, but not limited to servos, gears, links, springs, etc., to facilitate engagement between jaw interlock 29 and jaw member 14 and/or cutting blade 17.

For example, and in one particular embodiment, jaw interlock 29 may be automatically activatable via controller 11 when controller 11 triggers an end-of-duty cycle command to terminate ultrasonic energy to cutting blade 17. In this particular embodiment, one or more drive rods (not explicitly shown) may be configured to engage one or both of the jaw member 14 and cutting blade 17. Specifically, the drive may couple to a servo (not explicitly shown) that is in operable communication with controller 11 and configured to translate the drive rod along the longitudinal axis "A-A." Translation of the drive rod distally causes a distal end of the drive rod to mechanically engage corresponding proximal ends of jaw member 14 and cutting blade 17. The mechanical engagement may be an indent/detent configuration or other suitable mechanical engagement.

In another embodiment, jaw interlock 29 may be manually activatable via switching mechanism 28, e.g., a dial 30. In this particular embodiment, controller 11 may be configured to provide an audio indicator "A" or a visual indicator "V" to a user when controller 11 triggers an end-of-duty cycle command to terminate ultrasonic energy to cutting blade 17. Dial 30 may be configured such that rotation thereof translates the drive rod along the longitudinal axis "A-A" to engage jaw interlock 29 with one or both of jaw member 14 and/or cutting blade 17. As described above, translation of the drive rod distally causes the distal end of the drive rod to mechanically engage corresponding proximal ends of jaw member 14 and cutting blade 17. The mechanical engagement may be an indent/detent configuration or other suitable mechanical engagement.

During use of one particular embodiment of the instrument 2, tissue may be positioned between jaw member 14 and cutting blade 17. Subsequently, trigger 7 may be depressed to activate the cutting blade 17 to treat tissue of interest.

Once tissue has been sufficiently treated, e.g., dissected, one or more of the aforementioned sensor(s) 23 may be utilized to detect one or more of the aforementioned operational parameters associated with instrument 2. For example, sensor 23 may be utilized to sense an impedance of tissue during treatment thereof and communicate the sensed tissue impedance to controller 11 to determine if predetermined threshold impedance has been reached.

If the predetermined threshold impedance has been reached, controller 11 may trigger an end-of-duty command to terminate ultrasonic energy to cutting blade 17, which, in turn, terminates vibration of cutting blade 17.

The unique configuration of sensor(s) 23 and controller 11 allows cutting blade 17 to operate without the likelihood of the tissue contacting surface 15 and/or laminate liner 25 wearing or breaking down. As a result thereof, the operative life of the jaw member 14, laminate liner 25 and/or cutting blade 17 is increased when compared to jaw members (and/or cutting blades) associated with conventional ultrasonic instruments.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising: a housing having an elongated shaft extending therefrom, the elongated shaft having a jaw member disposed at a distal end thereof, the jaw member movable between an open configuration and a clamping configuration and including a tissue contacting surface; a cutting blade extending from a distal end of the elongated shaft and operably coupled to the housing and adjacent the jaw member, the cutting blade configured to receive ultrasound energy to treat tissue; an acoustic sensor configured to detect an acoustic signature of the cutting blade contacting and vibrating against the tissue contacting surface of the jaw member of the ultrasonic surgical instrument; and a controller in operable communication with the acoustic sensor, the controller including a memory storing a predefined acoustic signature, the controller configured to compare the detected acoustic signature with the stored predefined acoustic signature and terminate delivery of ultrasonic energy to the cutting blade upon the comparison to inhibit continued contact and vibration of the cutting blade against the jaw member, thereby inhibiting damage to the tissue contacting surface of the jaw member of the ultrasonic surgical instrument.

2. The ultrasonic surgical instrument according to claim 1, wherein the acoustic sensor is operably coupled to at least one of the jaw member or cutting blade.

3. The ultrasonic surgical instrument according to claim 1, further comprising at least one sensor configured to sense at least one operational parameter of the ultrasonic surgical instrument, the at least one sensor is one of a position sensor, a strain gauge sensor, a jaw sensor, a temperature sensor, or an impedance sensor.

4. The ultrasonic surgical instrument according to claim 3, wherein the at least one operational parameter associated with the ultrasonic surgical instrument includes a change in tissue impedance of tissue being treated, a change in resistance associated with the cutting blade contacting the tissue contacting surface of the jaw member, a change in an amount of ultrasonic power required to treat tissue, a spatial relationship between the jaw member and cutting blade, or a change in contact pressure between the jaw member and the cutting blade.

5. The ultrasonic surgical instrument according to claim 1, wherein the controller is a component of a generator of the ultrasonic surgical instrument.

6. The ultrasonic surgical instrument according to claim 1, wherein the tissue contacting surface of the jaw member is coated with at least one lubricious material.

7. The ultrasonic surgical instrument according to claim 6, wherein the at least one lubricious material is selected from a group consisting of polytetrafluoroethylene and silicone.

8. The ultrasonic surgical instrument according to claim 1, further including a jaw interlock activatable when delivery of ultrasonic energy to the cutting blade is terminated and configured to engage at least one of the jaw member or cutting blade to prevent contact therebetween.

9. An ultrasonic surgical system, comprising:
an ultrasonic surgical instrument, comprising:
a housing having a shaft extending therefrom, the shaft having a jaw member disposed at a distal end thereof, the jaw member including a tissue contacting surface;
a cutting blade extending from a distal end of the shaft and operably coupled to the housing and adjacent the jaw member to treat tissue; and
an acoustic sensor configured to detect an acoustic signature result of the cutting blade contacting and vibrating against the tissue contacting surface of the jaw member of the ultrasonic surgical instrument; and
a controller in operable communication with the acoustic sensor, the controller including a memory storing a predefined acoustic signature, the controller configured to compare the detected acoustic signature with the stored predefined acoustic signature and terminate delivery of ultrasonic energy to the cutting blade based upon the comparison to inhibit continued contact and vibration of the cutting blade against the jaw member, thereby inhibiting damage to the tissue contacting surface of the jaw member of the ultrasonic surgical instrument.

10. The ultrasonic surgical system according to claim 9, wherein the acoustic sensor is operably disposed on at least one of the jaw member or cutting element.

11. The ultrasonic surgical system according to claim 9, further comprising at least one sensor configured to sense at least one operational parameter of the ultrasonic surgical instrument, the at least one sensor is one of a position sensor, a strain gauge sensor, a jaw sensor, a temperature sensor, or an impedance sensor.

12. The ultrasonic surgical system according to claim 11, wherein the controller is configured to provide one of an audio and visual indication to a user when the operational parameter is sensed by the at least one sensor.

13. The ultrasonic surgical system according to claim 11, wherein the at least one operational parameter associated with the ultrasonic surgical instrument includes a change in tissue impedance of tissue being treated, a change in resistance associated with the cutting blade contacting the tissue contacting surface of the jaw member, a change in an amount of ultrasonic power required to treat tissue, a spatial relationship between the jaw member and cutting blade, or a change in contact pressure between the jaw member and the cutting blade.

14. The ultrasonic surgical system according to claim 9, wherein the controller is a component of a generator of the ultrasonic surgical instrument.

15. The ultrasonic surgical system according to claim 9, wherein the ultrasonic surgical instrument further includes a jaw interlock activatable when delivery of ultrasonic energy to the cutting blade is terminated and configured to engage at least one of the jaw member or cutting blade to prevent physical contact therebetween.

16. The ultrasonic surgical system according to claim 15, wherein the jaw interlock is manually activatable via a switch on the ultrasonic surgical instrument.

17. The ultrasonic surgical system according to claim 15, wherein the jaw interlock is automatically activatable via the controller.

18. The ultrasonic surgical system according to claim 9, wherein the controller is in operable communication with an audio detection module of the generator, the audio detection module configured to receive audio input from a speaker on the ultrasonic surgical instrument to detect a change in the acoustic signature of the ultrasonic surgical instrument.

19. The ultrasonic surgical system according to claim 9, wherein the tissue contacting surface of the jaw member is coated with at least one lubricious material.

20. The ultrasonic surgical system according to claim 19, wherein the at least one lubricious material is selected from a group consisting of polytetrafluoroethylene and silicone.

* * * * *